United States Patent
Eisenbach-Schwartz et al.

(10) Patent No.: US 9,314,483 B2
(45) Date of Patent: Apr. 19, 2016

(54) HUMAN MONOCYTE SUB-POPULATION FOR TREATMENT OF CENTRAL NERVOUS SYSTEM INJURY

(71) Applicant: YEDA RESEARCH AND DEVELOPMENT CO., LTD., Rehovot (IL)

(72) Inventors: Michal Eisenbach-Schwartz, Rehovot (IL); Ester Yoles, Rehovot (IL); Ravid Shechter, Rehovot (IL); Omer Miller, Rehovot (IL)

(73) Assignee: Yeda Research and Development Co., Ltd., Rehovot (IL)

(*) Notice: Subject to any disclaimer, the term of this patent is extended or adjusted under 35 U.S.C. 154(b) by 0 days.

(21) Appl. No.: 14/303,212

(22) Filed: Jun. 12, 2014

(65) Prior Publication Data

US 2014/0363411 A1 Dec. 11, 2014

Related U.S. Application Data

(63) Continuation of application No. PCT/IL2012/050522, filed on Dec. 13, 2012.

(60) Provisional application No. 61/570,593, filed on Dec. 14, 2011.

(51) Int. Cl.
| | |
|---|---|
| *C12N 5/0786* | (2010.01) |
| *A61K 35/15* | (2015.01) |
| *A61K 35/14* | (2015.01) |
| *A61K 35/12* | (2015.01) |

(52) U.S. Cl.
CPC ............... *A61K 35/15* (2013.01); *A61K 35/14* (2013.01); *C12N 5/0645* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 5,800,812 A | 9/1998 | Eisenbach-Schwartz et al. | 424/93.7 |
| 6,117,424 A | 9/2000 | Eisenbach-Schwartz et al. | 424/93.7 |
| 6,267,995 B1 | 7/2001 | Zheng et al. | 424/773 |
| 8,377,692 B2 * | 2/2013 | Fulga et al. | 435/377 |

FOREIGN PATENT DOCUMENTS

| | | | |
|---|---|---|---|
| WO | WO 98/05795 | 2/1998 | ............ C12Q 1/68 |
| WO | WO 03/044037 | 5/2003 | |
| WO | WO 2014/188436 | * 11/2014 | |

OTHER PUBLICATIONS

Donnelly, D.J., et al., "Deficient CX3CRI signaling promotes recovery after mouse spinal cord injury by limiting the recruitment and activation of Ly6Clo/iNOS+macrophages" *The Journal of Neuroscience* 31(27):9910-9922 (2011).
Ingersoll, M.A., et al., "Comparison of gene expression profiles between human and mouse monocylcte subsets" *Blood* 116(5): 857 (2010).
International Search Report issued in corresponding foreign application, pp. 1-4 (Mar. 18, 2013).
International Preliminary Report on Patentability issued in corresponding foreign application, pp. 1-9 (Jun. 17, 2014).
Schwartz M., "'Tissue-repairing' blood-derived macrophages are essential for healing of the injured spinal cord: From skin-activated macrophages to infiltrating blood-derived cells" *Brain, Behavior, and Immunity* 24(7): 1054-1057 (2010).
Shechter R., et al., "Infiltrating blood-derived macrophages are vital cells playing an anti-inflammatory role in recovery from spinal cord injury in mice" *PLoS Med* 6(7): 1-17 (2009).
Written Opinion issued in corresponding foreign application, pp. 1-8 (Mar. 18, 2013).

* cited by examiner

*Primary Examiner* — Ralph Gitomer
(74) *Attorney, Agent, or Firm* — J. Peter Paredes; Rosenbaum IP, P.C.

(57) ABSTRACT

A subpopulation of peripheral blood mononuclear cells (PBMCs) that is substantially devoid of $CD3^+$ cells, $CD19^+$ cells, $CD56^+$ cells and optionally of $CD16^+$ cells, for use in treatment of CNS injury is provided.

10 Claims, 8 Drawing Sheets

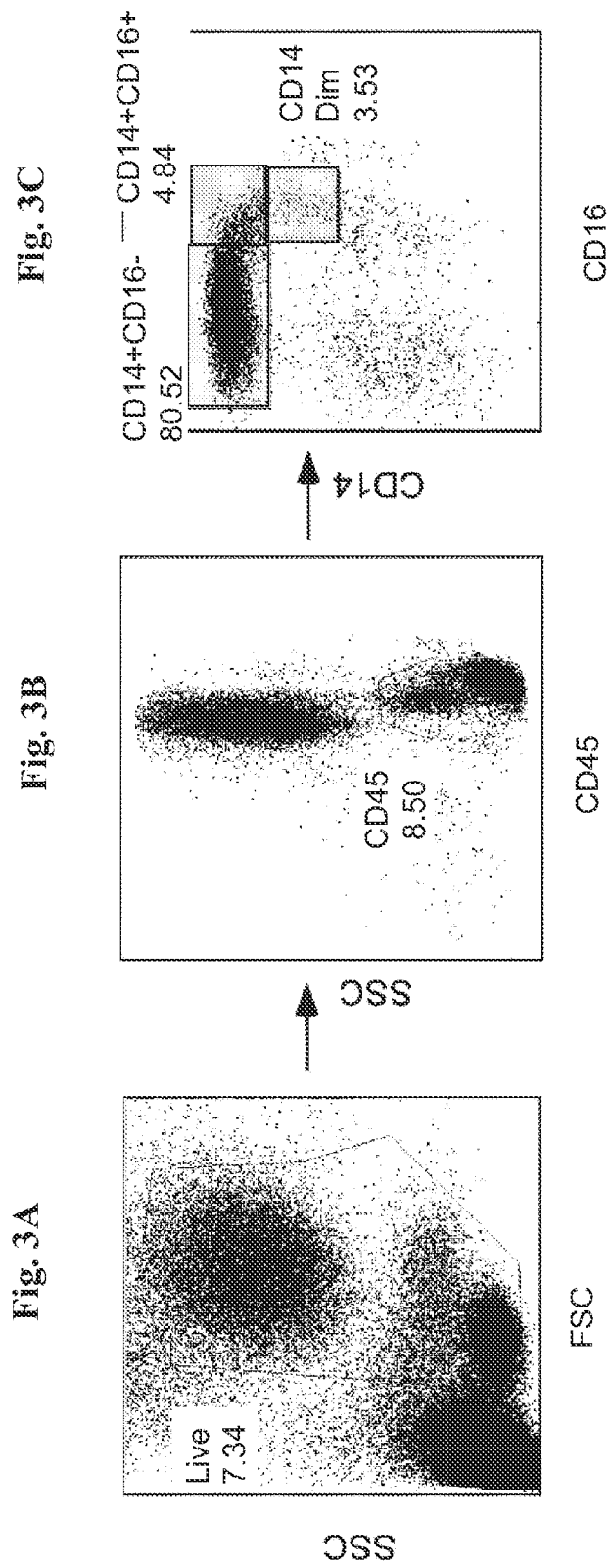

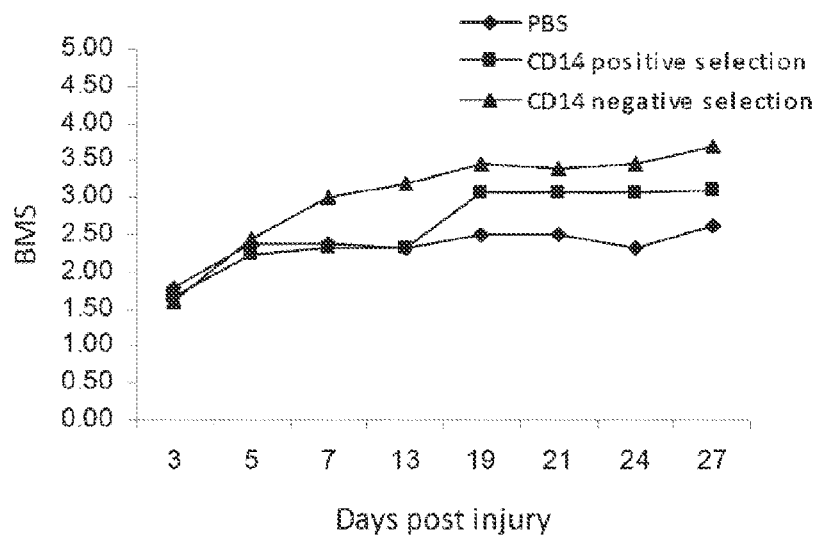
Fig. 7
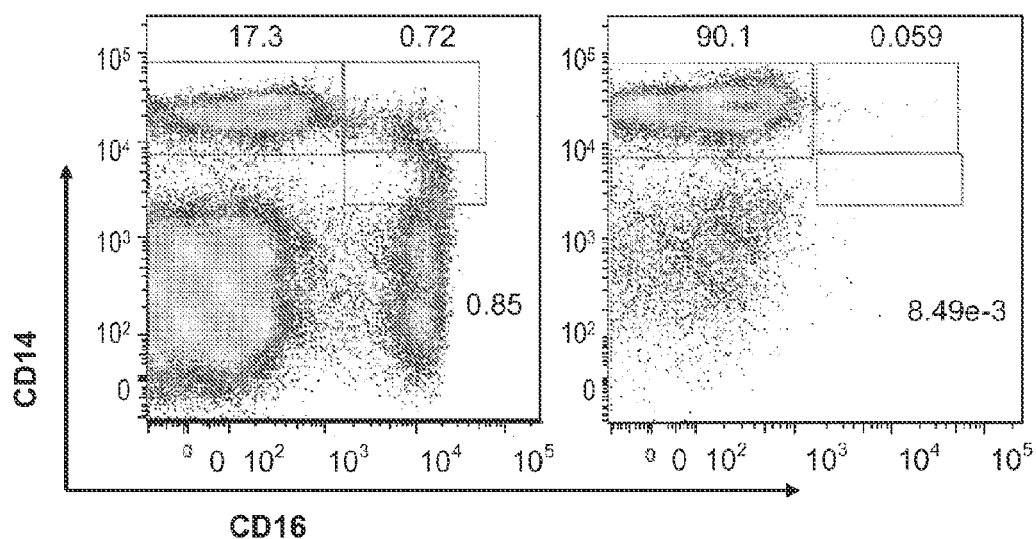
Fig. 8A                    Fig. 8B

HUMAN MONOCYTE SUB-POPULATION FOR TREATMENT OF CENTRAL NERVOUS SYSTEM INJURY

CROSS-REFERENCE TO RELATED APPLICATIONS

The present application claims priority to and is a continuation from PCT Application No. PCT/IL2012/050522, filed Dec. 13, 2012, which claims priority from U.S. Provisional Application Ser. No. 61/570,593, filed Dec. 14, 2011, all of which are herein incorporated by reference in their entireties.

FIELD OF THE INVENTION

The present invention relates in general to central nervous system (CNS) injuries and, in particular, to sub-populations of human monocytes useful in the treatment of CNS injuries, methods for isolation of these sub-populations and treatment of patients suffering from spinal cord injury.

BACKGROUND OF THE INVENTION

Central nervous system injuries, including injuries to the spinal cord, are among the most devastating and disabling injuries possible. Depending upon the severity of the injury, paralysis of varying degrees can result. Paraplegia and quadriplegia often result from severe injury to the spinal cord.

The worldwide annual incidence of spinal cord injury (SCI) is estimated at 22 persons per million and the total number of SCI survivors is estimated at 2.5 million. SCI most often occurs in people in their mid-twenties who can anticipate a quasi-normal life expectancy albeit with challenges to maintain an acceptable quality of life. This generates important personal, societal, and economic costs. Although life expectancy is very good, SCI patients suffer from some important handicaps (depending on the level and severity of the lesion) that seriously diminish their quality of life (e.g., paralysis, sensory loss, intractable pain, pressure sores, and urinary and other infections). Despite the intensive work that has been invested by the scientific and clinical communities during the last two decades, there is as yet no cure or treatment that can reverse lost functions after SCI.

To date, the therapeutic efforts focused mainly on preventing the destructive events (neuroprotection) and less on augmenting the spontaneous repair events evoked by SCI. Further recovery of function will require a combination of effective neuroprotective and restorative therapeutic interventions. The above considerations have led the inventors to follow a novel physiological approach that employs the body's professional healing system, the immune system, to contend with the consequences of central nervous system (CNS) damage leading to neuroprotection and restoration.

It was shown in the laboratory of the inventors that blood-derived monocytes incubated with skin segments acquired a non-inflammatory phenotype similar to anti-inflammatory M2 monocytes described in the literature (Bomstein et al., 2003). Injection of the monocytes into the injured spinal cord induced better recovery from SCI in rats (U.S. Pat. No. 5,800,812; U.S. Pat. No. 6,117,424; and U.S. Pat. No. 6,267,955). This approach was tested in a clinical study on patients suffering from acute sever spinal cord injury showing encouraging results (WO 03/044037; Knoller et al., 2005). Accordingly, the treatment required a surgical procedure including laminectomy to expose the injured spinal cord and injection of the cells to the borders of the lesion site, which was difficult to allocate. The inventors felt that finding ways to overcome the difficulty of allocating the site of lesion and the exposure of patients to an invasive procedure would be helpful in the treatment of SCI.

More recent research performed in the laboratory of the inventors showed that following spinal cord injury, at three to four days post injury blood born monocytes spontaneously infiltrate to the damaged CNS, preferentially accumulate at the margins of the lesion site and play a pivotal role in the process of recovery. These cells modulate the immune activity at the injured tissue to become less inflammatory, and produce molecules that support healing, and thus favorable for cell renewal and tissue repair (Shechter et al., 2009). Despite their positive role, in severe injuries it was insufficient to induce a full recovery or even partial functional recovery.

Infiltration/recruitment of peripheral blood into the lesion site is controlled by signals elicited from the lesion site, which affects the brain-CSF barrier. The limited spontaneous recovery following CNS injury can be attributed in part to the inadequate, untimely, spontaneous recruitment of the effective subset of monocytes to the lesion site. In line with this, we have shown that enrichment of peripheral blood monocytic pool with bone-marrow derived CD115 cells augmented functional recovery following SCI in mice (Shechter et al., 2009).

Blood monocytes are heterogenic cellular population with different characteristics and activities. Utilizing blood monocytes for therapeutic purposes requires the identification of the cells with harmful functions and those that are beneficial.

In humans, it was proposed that the expression of CD16 on monocytes can distinguish between three subsets, namely CD14++CD16− (classical) CD14++CD16++ and CD14dimCD16++ (non-classical) monocytes, but their role in physiological and pathological conditions is not fully understood.

SUMMARY OF INVENTION

In some aspects, the present invention provides a subpopulation of peripheral blood mononuclear cells (PBMCs) substantially devoid of $CD3^+$ cells, $CD19^+$ cells and $CD56^+$ cells, or a subpopulation of PBMCs substantially devoid of $CD3^+$ cells, $CD19^+$ cells, $CD56^+$ cells and $CD16^+$, for use in treatment of central nervous system (CNS) injury.

In other aspects, the present invention provides compositions comprising a subpopulation of PBMCs substantially devoid of $CD3^+$ cells, $CD19^+$ cells and $CD56^+$ cells, or a subpopulation of PBMCs that is substantially devoid of $CD3^+$ cells, $CD19^+$ cells, $CD56^+$ cells and $CD16^+$, for treatment of CNS injury.

In yet other aspects, the present invention relates to methods for treating a CNS injury comprising administering to an individual in need an effective amount of a subpopulation of PBMCs substantially devoid of $CD3^+$ cells, $CD19^+$ cells and $CD56^+$ cells, or a subpopulation of PBMCs substantially devoid of $CD3^+$ cells, $CD19^+$ cells, $CD56^+$ cells and $CD16^+$ cells. The cells are preferably injected to the CSF via lumbar puncture or the Cisterna Magna.

In other aspects, the present invention provides methods for isolation of a subpopulation of human PBMC from blood substantially devoid of $CD3^+$ cells, $CD19^+$ cells and $CD56^+$ cells or of a subpopulation of human PMBC substantially devoid of $CD3^+$ cells, $CD19^+$ cells, $CD56^+$ cells and $CD16^+$ cells.

BRIEF DESCRIPTION OF DRAWINGS

FIGS. 3A-D show distribution of peripheral blood monocytes according to their expression of CD14, CD16 and CD115. FIG. 3A shows distribution of total live monocyte population as measured by FACS (the delineated cells are the live cells (live gate). SSC, side scatter; FSC, forward scatter; FIG. 3B shows distribution of CD45 positive cells out of the total live gate., i.e. cells of hematopoietic origin (except erythroid cells, platelets, and their precursor cells). FIG. 3C shows that monocytes (out of the monocyte sub-population delineated from the CD45 positive cells) labeled by monoclonal anti-CD14 and anti-CD16 antibodies can be separated into three distinct subpopulations: $CD14^+CD16^-$ (80.5%), $CD14^+CD16^+$ (4.8%) and $CD14^{dim}CD16^+$ (3.5%). FIG. 3D shows the expression level (in Mean Fluorescence Intensity) of CD115 on the different monocyte sub-populations.

FIG. 7 shows that ICV injection of blood derived monocytes isolated by negative selection on day 4 post injury improve functional recovery in mice. Yet, blood derived monocytes isolated by positive selection of CD14 positive cells was less beneficial. BMS, Basso Mouse Scale.

FIGS. 8A-B show a sequential approach for the isolation of CD14++CD16− cells i.e. first depletion of the leukocytes using CD3, CD19 and CD56 antibodies (A), followed by depletion of the CD16 positive cells. The final product is a population comprising CD14++CD16− cells and less than 0.1% of CD16+ cells (B).

DETAILED DESCRIPTION OF THE INVENTION

Figure 1:
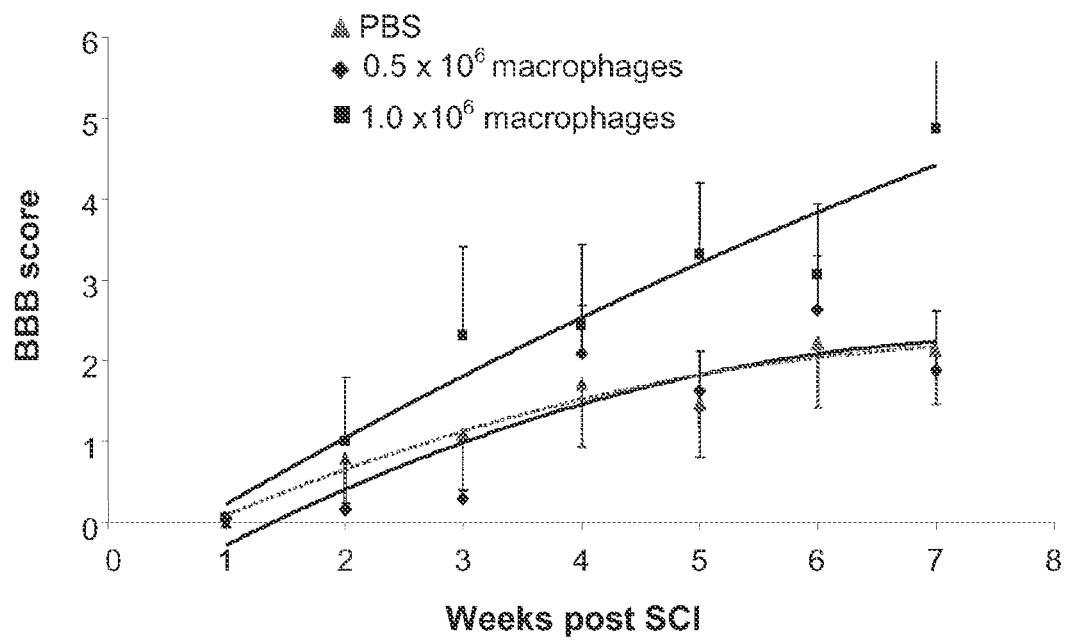
FIG. 1 shows that lumbar puncture (LP) injection of skin-activated macrophages promotes functional recovery in rats following severe spinal cord injury. Wild-type rats were subjected to severe spinal cord injury (SCI). After 8 days, the injured animals were injected with $0.5\times10^6$ or $1\times10^6$ skin-activated macrophages or with vehicle into the CSF (cerebrospinal fluid) via LP. A significant improvement in locomotion, represented by an increase in the Basso-Beattie-Bresnahan (BBB) score was observed in the group of animals injected with the higher dose of macrophages.

The present invention is based on the finding that a subpopulation of monocytes that is defined by the absence, or near absence, of cells expressing CD3, CD19, CD56 and optionally CD16, is capable of homing from the cerebrospinal fluid (CSF) to the site of injury in the spinal cord, and promote there tissue restoration and improved functional recovery. The methods of the prior art teach the necessity of administering mononuclear phagocytes accurately to the borders of the lesion in order to obtain satisfactory efficacy (for example U.S. Pat. No. 5,800,812).

It has further been found in accordance with the present invention that the beneficial effect of the cells in healing the wounded spinal cord is obtained either by administering cells activated by co-incubation with a piece of skin or by administering un-activated cells into the CSF of injured spinal cord.

A cell expressing on its surface a certain identifiable marker, such as a Cluster of Differentiation (CD) molecule X is referred to herein as CD $X^+$. For example, a cell expressing on its surface a CD3 molecule is referred to herein as $CD3^+$. The relative amount of the CD molecule expressed on the cell surface is referred to by adding "+", e.g. $CD3^{++}$ for high amounts of CD molecules, or the term "dim", showing a relative low level of CD molecules. A population of cells comprising a cell type defined by the expression of a certain CD, a population relatively enriched with these cells, or a population lacking such cells, is designated $CD^+$, $CD^{++}$ or $CD^+$, respectively.

Thus, in certain embodiments, the subpopulation of peripheral blood mononuclear cells (PBMCs) is substantially devoid of $CD3^+$ cells, $CD19^+$ cells and $CD56^+$ cells.

In other embodiments, also $CD16^+$ cells have been removed from the PBMC sub-population resulting in a subpopulation of PBMCs that is further substantially devoid of $CD16^+$ cells, i.e. a subpopulation substantially devoid of $CD3^+$ cells, $CD19^+$ cells, $CD56^+$ cells and $CD16^+$ cells.

The term "peripheral blood mononuclear cell (PBMC)" as used herein refers to any blood cell having a round nucleus, such as a lymphocyte, a monocyte or a macrophage. Methods for isolating PBMCs from blood are readily apparent to those skilled in the art. An non-limiting example is the extraction of these cells from whole blood using ficoll, a hydrophilic polysaccharide that separates layers of blood, with monocytes and lymphocytes forming a buffy coat under a layer of plasma or by leukapheresis, the preparation of leukocyte concentrates with the return of red cells and leukocyte-poor plasma to the donor The phrase "a population of cells substantially devoid of" is used herein interchangeably with the phrase "near absence of" and preferably includes a population of cells lacking a certain cell type, or alternatively comprising a relative amount of a certain cell type not exceeding about 0.05%, 0.1%, 0.5%, 1%, 2%, 3%, 4%, or 5% of the total number of cells in said population of cells.

Thus, in certain embodiments, the relative amount of each one of $CD3^+$ cells, $CD19^+$ cells and $CD56^+$ cells is not exceeding about 0.05%, 0.1%, 0.5%, 1%, 2%, 3%, 4%, or 5% of the total number of cells in the PBMC population. In certain embodiments, the relative amount of $CD16^+$ cells in the subpopulation substantially devoid of $CD3^+$ cells, $CD19^+$ cells, $CD56^+$ cells and $CD16^+$ cells is not exceeding about 0.05%, 0.1%, 0.5%, 1%, 2%, 3%, 4%, or 5% of the total number of cells.

In certain embodiments, the subpopulations substantially devoid of $CD3^+$ cells, $CD19^+$ cells and $CD56^+$ and optionally also substantially devoid of $CD16^+$ cells, are substantially enriched in $CD14^+$ cells.

The phrase "a population of cells substantially enriched in" refers to a population of cells comprising a relative amount of a certain cell type exceeding about 60%, 70%, 80%, 90%, 95% or 99% of the total number of cells in said population of cells.

In certain embodiments, the subpopulation of PBMCs substantially devoid of $CD3^+$ cells, $CD19^+$ cells and $CD56^+$ cells comprises at least about 60% $CD14^+$ cells, and the subpopulation substantially devoid of $CD3^+$ cells, $CD19^+$ cells, $CD56^+$ cells and $CD16^+$ cells comprises at least about 80% $CD14^+$ cells. Thus, the subpopulation substantially devoid of $CD3^+$ cells, $CD19^+$ cells, $CD56^+$ cells and $CD16^+$ cells is also referred to herein as a $CD14^{++}$, $CD16^+$ population.

In certain embodiments, the subpopulation of PBMCs of the present invention is for use in treatment of neuronal degeneration caused by the CNS injury.

Consequently, in certain embodiments, the subpopulation of PBMCs of the present invention may be for use in treatment of spinal cord injury, and the treatment may comprise promotion of spinal cord tissue restoration, functional recovery, or both.

In other embodiments, the CNS injury is trauma such as blunt trauma, penetrating trauma, brain coup or contrecoup, trauma sustained during a neurosurgical operation or other procedure, or stroke such as hemorrhagic stroke or ischemic stroke.

In a different embodiment, the subpopulation of human PBMCs is isolated from autologous PBMCs, i.e. blood is collected from a patient in need of treatment of CNS injury, a PBMC subpopulation according to the present invention is prepared as defined herein below, and then administered back to the patient.

In another embodiment, the subpopulation of human PBMCs is isolated from allogeneic PBMCs, i.e. blood is collected from a genetically similar, but not identical, donor, a PBMC subpopulation according the present invention is prepared as defined herein below and optionally stored in a cell-bank before being administered to the patient.

In certain embodiments, the subpopulation of PBMCs is formulated for injection, preferably for injection into the CSF.

As used herein, the term "pharmaceutically acceptable carrier" refers to a non-toxic, diluent, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyllaurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

These additional inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990), and *Remington's Pharmaceutical Sciences*, 18th Ed., Mack Publishing Co., Easton, Pa. (1990), both of which are incorporated by reference herein in their entirety.

In another aspect, the present invention provides a composition comprising a subpopulation of PBMCs as defined herein above for use in treatment of CNS injury. The composition may comprise cells of a subpopulation of PBMCs suspended in a pharmaceutically acceptable carrier adapted for injection, preferably for administration into the CSF. A non-limiting example of a pharmaceutically acceptable carrier is PBS or a culture medium. However, alternative pharmaceutically acceptable carriers will readily be apparent to those skilled in the art.

In certain embodiments, the administration of the cells or the composition into the CSF is via intrathecal injection, lumbar puncture (LP), injection through the Cisterna Magna (CM), intracerebroventricular (ICV) injection, or a combination thereof.

It has further been found in accordance with the present invention that the PBMC subpopulation successfully migrate from the CSF to the boundaries of an injury in the spinal cord, mitigates the injury and improve functional recovery, whether the cells have previously been activated by co-culture with a piece of skin, i.e. they are skin-activated cells, or whether they are naïve, i.e. not manipulated or non-activated.

Thus, in certain embodiments, the cells of the subpopulation of PBMCs of the present invention injected into the CSF are skin-activated cells.

In other embodiments, the cells of the subpopulation of PBMCs of the present invention injected into the CSF are non-activated cells.

The subpopulation of PBMCs according to the present invention, and the composition comprising them, are useful for treatment of CNS injury, such as spinal cord injury. In particular, the treatment comprises promotion of spinal cord tissue restoration including, for example, preventing or inhibiting neuronal degeneration, promotion of neuronal survival, axonal regeneration and/or sprouting, neurogenesis in an injured spinal cord, and/or promotion of functional recovery, as measured for example by the Basso-Beattie-Bresnahan (BBB) score in rats or the Basso Mouse Scale (BMS) in mice, as defined herein below.

In another embodiment, the CNS injury may be trauma, such as blunt trauma, penetrating trauma, brain coup or contrecoup, trauma sustained during a neurosurgical operation or other procedure, or stroke such as hemorrhagic stroke or ischemic stroke.

Accordingly, the present invention further provides a method for treating a CNS injury, particularly a spinal cord injury, comprising administering to an individual in need an effective amount of a subpopulation of peripheral blood mononuclear cells (PBMCs) as defined herein.

As used herein, the terms "treatment" or "treating" of an injury encompasses alleviation of at least one symptom thereof, a reduction in the severity thereof, or the delay, prevention, or inhibition of the progression thereof. Treatment need not mean that the injury is totally cured. To be an effective treatment, a useful composition herein needs only to reduce the severity of an injury, reduce the severity of symptoms associated therewith or provide improvement to a patient or subject's quality of life.

In a different aspect, the present invention provides a method for isolation of a subpopulation of human PMBC from blood that is substantially devoid of $CD3^+$ cells, $CD19^+$ cells and $CD56^+$ cells, comprising the steps: (i) isolating mononuclear cells from blood; and (ii) removing the $CD3^+$ cells, CD19+ cells and CD56+ cells from the mononuclear cells of (i) by contacting said mononuclear cells with anti-CD3+ antibodies, anti-CD19+ antibodies and anti-CD56+ antibodies, each one of which is linked to microbeads, thereby binding said cells to said microbeads, and removing the microbeads, thereby obtaining a subpopulation of human peripheral blood mononuclear cells (PMBC) from blood that is substantially devoid of CD3+ cells, CD19+ cells and CD56+ cells.

In a still different aspect, the present invention provides a method for isolation of a subpopulation of human peripheral blood mononuclear cells (PMBC) from blood that is substantially devoid of CD3+ cells, CD19+ cells, CD56+ cells and CD16+ cells, comprising the steps: (iii) isolating mononuclear cells from blood; and (iv) removing the CD3+ cells, CD19+ cells, CD56+ cells and CD16+ cells from the mononuclear cells of (iii) by contacting said mononuclear cells with anti-CD3+ antibodies, anti-CD19+ antibodies, anti-CD56+ antibodies and anti-CD16+ antibodies, each one of which is linked to microbeads, thereby binding said cells to said microbeads, and removing the microbeads, thereby obtaining a subpopulation of human PMBC from blood that is substantially devoid of CD3+ cells CD19+ cells, CD56+ cells and CD16+.

In certain embodiments, step (iv), i.e. the removal of CD3+ cells, CD19+ cells, CD56+ cells and CD16+, comprises the sub-steps: (v) removing the CD3+ cells, CD19+ cells and CD56+ cells from the mononuclear cells of (iii) thereby obtaining a subpopulation of human PMBCs from blood that is substantially devoid of CD3+ cells CD19+ cells and CD56+ cells; and (vi) removing the CD16+ cells from the PMBC population of (v), thereby obtaining a subpopulation of human PMBC from blood that is substantially devoid of CD3+ cells CD19+ cells, CD56+ cells and CD16+ cells.

In one embodiment, the step (iv) is performed in a single step.

The antibodies that capture the cells expressing the desired antigen on their surface, such as CD3, CD19, CD56 and/or CD16, may be biotinylated and then linked to microbeads comprising avidin or streptavidin or equivalent biotin-binding proteins, or the antibodies may be supplied to the cells when already bound to microbeads. The microbeads may be magnetic or non-magnetic and the cells, when bound to the microbeads, may be removed from the solution in which the cells are suspended, by centrifugation, if the microbeads are not magnetic, or by exposure to the magnetic field of a magnet, if they are.

In preferred embodiments, the antibodies are linked to magnetic microbeads when brought in contact with the cells and the cells are removed by removing the microbeads to which the cells are bound by pulling them from the solution with a magnet.

The invention will now be illustrated by the following non-limiting examples.

EXAMPLES

Material and Methods (i) Animals. The animals used in the experiments, if not indicated differently, were supplied by Harlan Laboratories, ISO accredited SPF Laboratory Animal breeder in Israel, and the Animal Breeding Center of the Weizmann Institute of Science (Rehovot, Israel). All animals were handled according to the regulations formulated by the Weizmann Institute's Animal Care and Use Committee.

(ii) Spinal cord injury. Rats (wild-type Sprague-Dawley rats) were anesthetized (Ketamine 70 mg/kg, Bedford Laboratories, OH, US, Xylazine 10 mg/kg, VMP, Bioulab, France), laminectomized at T9, and contused using a NYU impactor (Gruner (1992) A monitored contusion model of spinal cord injury in the rat. J Neurotrauma. Summer; 9(2): 123-6; discussion 126-8. Review) to drop a 10 g metal rod from height of 50 mm onto the exposed spinal cord (considered to cause severe damage). Mice were anesthetized, their spinal cords were exposed by laminectomy at T12, and a force of 200 kdyn was placed for is on the laminectomized cord using the Infinite Horizon spinal cord impactor (Precision Systems and Instrumentation, Lexington, Ky.), a device shown to inflict a well-calibrated contusive injury of the spinal cord.

(iii) Skin preparation and coincubation with monocytes. Small pieces of skin (2×6 mm) were prepared from the backs of the same donor rats that had been bled to prepare the monocytes. The fur on the upper back was shaved and the skin was sterilized with ethanol before cutting. Two pieces of the skin tissue were placed with $5 \times 10^6$ cells of the homologous monocyte fraction (see above) in 5 ml DCCM-1 (Biological Industries, Beit HaEmek, Israel) and incubated for 16 h at 37° C., 5% $CO_2$. At the end of incubation, the skin pieces were removed and the cells recovered by centrifugation.

(v) BBB Score: behavioral analysis in the rats was performed using the open-field locomotion Basso-Beattie-Bresnahan (BBB) score [Basso, D.M., Beattie, M.S. & Bresnahan, J.C. A sensitive and reliable locomotor rating scale for open field testing in rats. J. Neurotrauma 12, 1-21 (1995).] Behavioral analysis in the mice was performed using the Basso Mouse Scale (BMS) for hind limb motor function assessment in open field [Basso DM, Fisher LC, Anderson AJ, Jakeman LB, McTigue DM, Popovich PG. Basso Mouse Scale for locomotion detects differences in recovery after spinal cord injury in five common mouse strains. J Neurotrauma. 2006 May; 23(5):635-59].

(vii) Statistical Analysis: Repeated measures ANOVA was used for the BBB and BMS scoring with follow-up comparison of treatments for each week by contrast t-test and correction for multiple comparison by the Holm method (p=0.05).

Example 1

Lumbar Puncture Injection of Skin-activated Macrophages Promotes Functional Recovery in Rats Following Severe Spinal Cord Injury At first, we were looking for a clinically feasible way to augment the number of blood-derived monocytes with the desired phenotype in the injured spinal cord using a minimally invasive way. We examined the efficacy of injecting skin-activated blood-derived monocytes into the cerebrospinal fluid (CSF) by lumbar puncture (LP), in reducing functional deficits following spinal cord injury in the rat.

TABLE 1

Functional recovery in rats following severe spinal cord injury

| Treatment | Total No. of animals | No. of animals recovered (BBB >6) | % recovery |
|---|---|---|---|
| PBS | 20 | 6 | 30% |
| 0.5 × 10⁶ MQ | 17 | 3 | 18% |
| 1 × 10⁶ MQ | 16 | 10 | 63% |

Wild-type Sprague-Dawley rats were subjected to severe spinal cord contusion (see Materials and Methods). After 8 days, the injured animals were injected into the CSF with $0.5 \times 10^6$ or $1 \times 10^6$ skin-activated macrophages (MQ) or with vehicle (PBS), via LP. A dose dependent effect was shown in facilitating motor recovery, with a significant improvement in locomotion observed for the group of animals injected with the highest dose of macrophages (FIG. 1, Table 1).

Example 2

Figure 2:
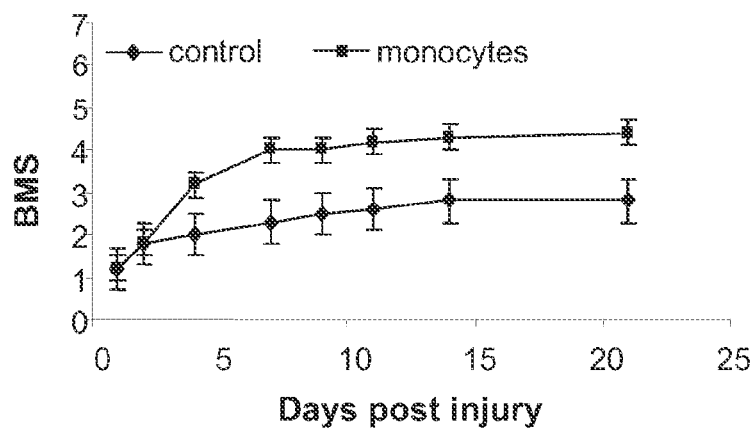
FIG. 2 shows that intracerebroventricular (ICV) injected monocytes provide for a significant improvement in locomotor activity in wild-type mice subjected to spinal cord injury (SCI). BMS, Basso Mouse Scale.

Injection of Non-Activated Bone-marrow Derived Mouse Monocytes into the CSF Promotes Functional Recovery in Mice Following Spinal Cord Injury Further we tested whether non-activated bone-marrow derived monocytes injected into the CSF via intracerebroventricles (ICV) would home to the injured spinal cord parenchyma. Wild-type mice were subjected to spinal cord contusion (see Materials and Methods). After 3 days, the injured animals were ICV injected with isolated green flourescent protein (GFP) expressing-naive bone marrow derived monocytes ($0.5 \times 10^6$ $Cx_3cr1^{GFP/+}$ monocytes), and analyzed for the presence of the injected cells at the site of injury. Immunohistochemical analysis of the injured site 4 days following injection revealed the presence of the injected GFP expressing cells in the injured parenchyma, in close proximity to the margins of the lesion site (not shown [See explanation at Brief Description of Drawings]. Similarly treated animals were followed for locomotor activity assessed by a motor scale (BMS): the augmentation of the monocyte pool resulted in recovery that exceeded spontaneous recovery levels as can be seen from the significant improvement in locomotion in the mice (FIG. 2).

These results suggested that non-activated bone marrow derived monocytes can home to injured parenchyma from the CSF, and therefore, that the blood-CSF barrier might be a route whereby monocytes spontaneously enter to damaged CNS.

Example 3

Isolation of Human Mononuclear Cells that Express High Level of $CX_3CR1$ and Low Level of CCR2 from PBMC In humans, three populations of monocytes are defined by the expression of CD14 and CD16, namely: $CD14^+CD16^-$, $CD14^+CD16^+$, and $CD14^{dim}CD16^+$. The $CD14^+CD16^+$ monocytes represent 80% to 90% of blood monocytes, and express high levels of the chemokine receptor CCR2 and low levels of the chemokine receptor $CX_3CR1$ (the receptor of Fractalkine). In contrast to this major subset, human CD16+ monocytes express high levels of $CX_3CR1$ and low levels of CCR2 (Cros et al., 2010). According to Cros et al (2010), gene expression analyses indicated similarities between human $CD14^{dim}CD16+$ and murine patrolling $Gr1^{dim}$ monocytes. The $CD14^{dim}CD16^+$ cells are bona fide monocytes involved in the innate local surveillance of tissues and the pathogenesis of autoimmune diseases.

SCHEME I

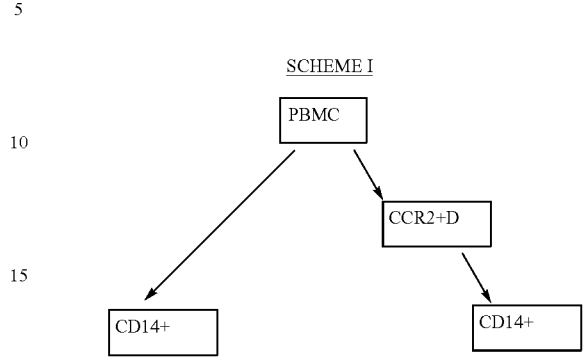

In order to isolate from peripheral blood mononuclear cells (PBMC) the $CD14^{dim}CD16+$ cells that express high level of $CX_3CR1$ and low level of CCR2, we used the combined method of negative selection of CCR2 ($CCR2^+$ depletion) and positive selection of $CD14^+$ ($CD14^+$) while isolation of $CD14^+$ from PBMC was used as control, as illustrated in scheme I.

3.1 Enriching CD14dimCD16+ Cell Population:

(i) Isolation of mononuclear cells from human peripheral blood: Fresh blood (8 ml) collected from healthy donor was diluted 1:1 with 2.5% FCS in PBS, and loaded on a Ficoll gradient (Ficoll-Paque plus, Amersham Biosciences). Tubes were centrifuged for 20 min at 1000 g, at 20° C. The mononuclear cell phase was collected and washed twice with PBS.

(ii) CCR2+ depletion: First the mononuclear cells were Fc-receptor-blocked by treatment with FcR blocking reagent (2.5 µl/$10^6$ cells) (130-059-901, Miltenyi Biotec) for 15 minutes at room temperature. Then, without washing, the monoclonal anti-human CCR2-biotin reagent (FAB151B, R&D Systems) was added (10 µl/$10^6$ cells) and incubated for 35 minutes at 2°-8° C. Then the cells were washed with cold MACS™ buffer (1 mM EDTA, 2% FCS in PBS) and streptavidin microbeads (130-048-101, Miltenyi Biotec) were added (20 µl/$10^7$ cells) for 20 minutes at 2°-8° C. The cells were washed and resuspended with 0.5 ml of MACS™ buffer. The depletion of the CCR2+ cells was done with LD column (130-042-901, Miltenyi Biotec) according to the manufacturers' protocols.

(iii) Isolation of CD14+ cells: The cells were resuspended with MACS™ buffer (80 µl/$10^7$ cells) and CD14+ microbeads (130-050-201, Miltenyi Biotec) were added (20 µl/$10^7$ cells) for 15 minutes at 2°-8° C. Then, the cells were washed and resuspended with 0.5 ml of MACS buffer. The positive selection of the CD14+ cells was done by using magnetic separation on LS column (130-042-401, Miltenyi Biotec) according to the manufacturer's protocols.

(iv) Fluorescence-activated cell sorting (FACS™) staining of human mononuclear cells All samples were stained according to the manufacturers' protocols. All samples were filtered through 70 µm nylon mesh and blocked with FCR blocking reagent (30 µl/$10^6$ cells) (130-059-901, Miltenyi Biotec) for 15 minutes at room temperature. The following fluorochrome-labeled anti-human monoclonal antibodies were used according to the manufacturers' protocols: PerCP conjugated anti CD45 (345809, BD), FITC conjugated anti CD115 (FAB329F, R&D Systems), Pacific Blue™ conjugated anti CD14 (BLG-325616), Alexa Fluor® 700 conjugated anti CD16 (BLG-302026), PE conjugated anti CX$_3$CR1 (MBL-D070-5) and PerCP conjugated anti CCR2 (BLG-335303).

3.2 Results

Figure 3D:
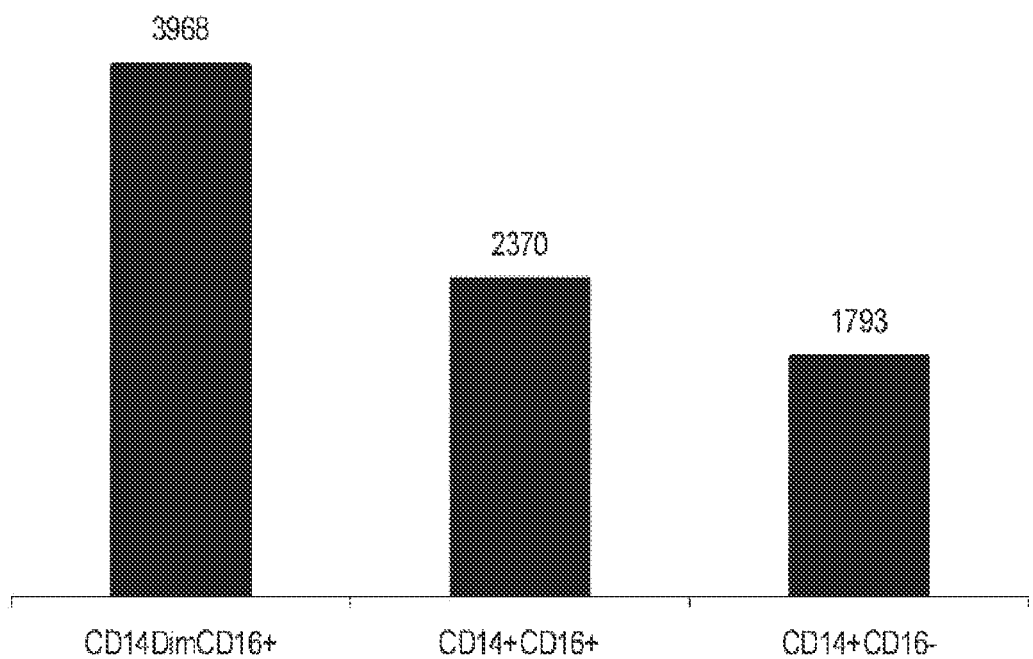
Figure 4A:
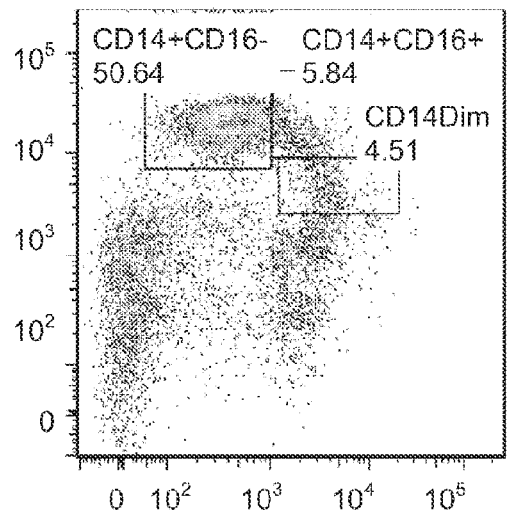
FIGS. 4A-E show distribution of $CX_3CR1$ and CCR2 on peripheral blood monocytes (4A) and on the three subpopulations of monocytes: $CD14^+CD16^-$ (4B), $CD14^+CD16^+$ (4C) and $CD14^{dim}CD16^+$ (4D). (4E) a graph showing the distribution in the three subpopulations.
Figure 4B:
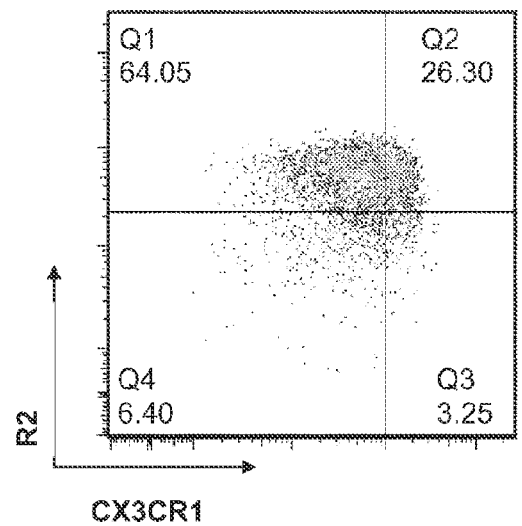
Figure 4C:
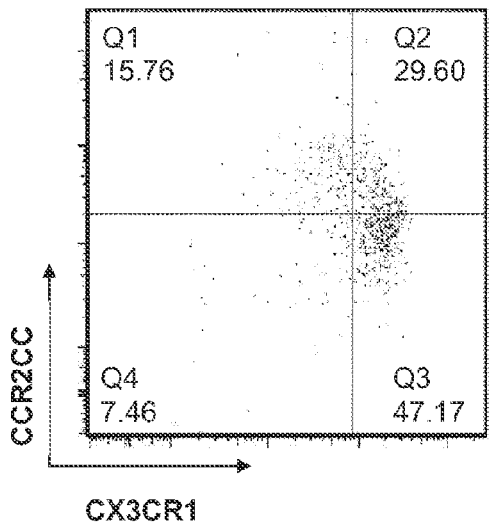
Figure 4D:
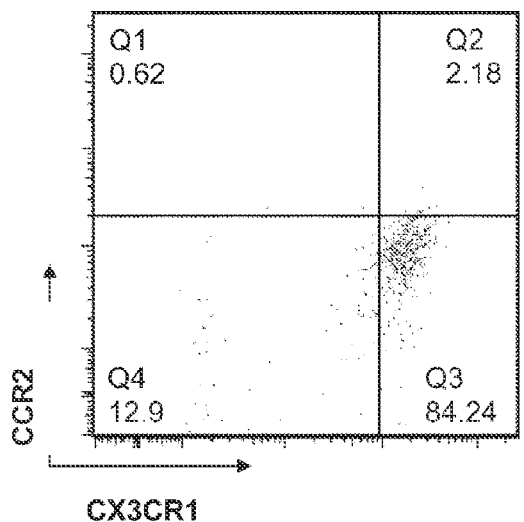
Figure 4E:
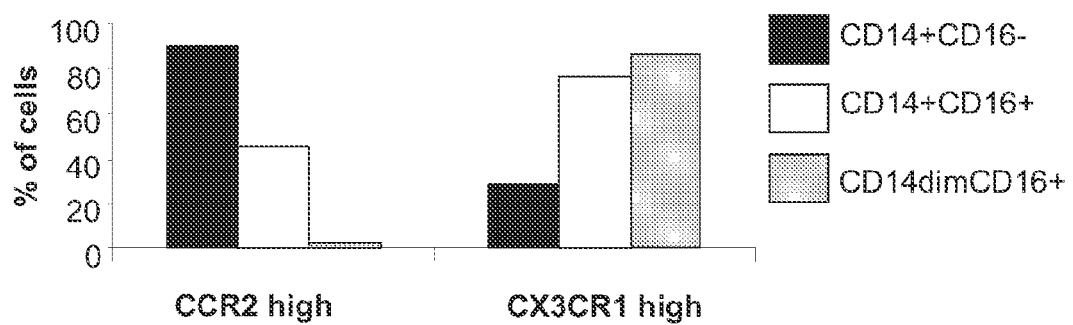

The monocyte population was analyzed out of the live cellular population (FIG. 3A) and identified using the site scatter distribution of the CD45+ cells (FIG. 3B), delineated by thin black line). The distribution of the monocyte subpopulation was presented by their CD14 and CD16 antigens expression (FIG. 3C). Analysis of the monocyte subpopulation from PBMC of healthy donor according to the CD14 and CD16 staining by FACS reveals the distribution of the following subpopulations: CD14$^+$CD16$^+$ (80.5%), CD14$^+$CD16$^+$ (4.8%) and CD14$^{dim}$CD16$^+$ (3.5%), FIGS. 3A-C. Interestingly, the subpopulation of the CD14$^{dim}$CD16$^+$ also stained with the marker CD115 that belongs to the CSF-1 receptor and characterizes the bone marrow derived monocytes (FIG. 3D).

Analysis of the monocyte subpopulation from PBMC of healthy donor according to the CCR2 and CX3CR1 staining by FACS revealed that monocytes that do not express CD16 (CD16− subpopulation) highly express CCR2 whereas monocytes that express CD16 (CD14+CD16+ and CD14dimCD16+ subpopulations) show low expression of CCR2 and high CX3CR1 (FIGS. 4A-E).

This result encouraged us to eliminate the subpopulation of CCR2+ cells in order to enrich the subpopulation of CD16+ cells.

Figure 5:
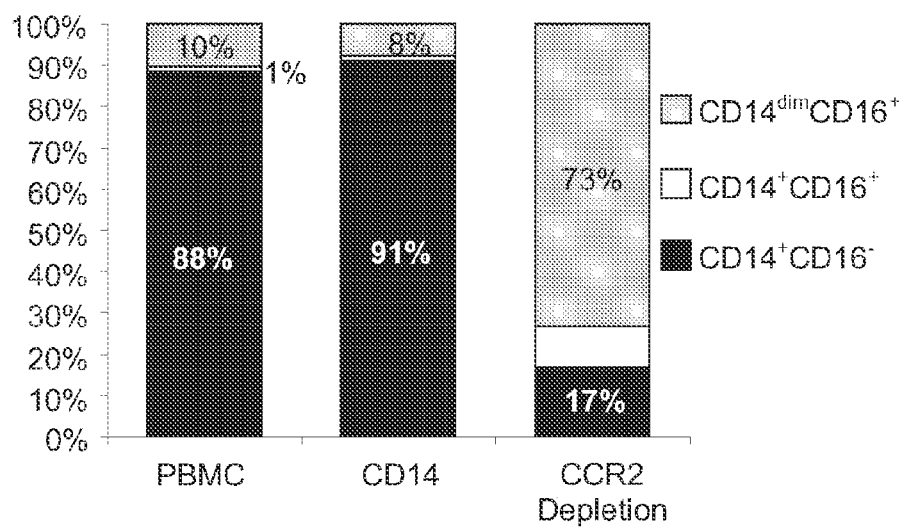
FIG. 5 shows enrichment of $CD14^{dim}CD16^+$ cells by depletion of the $CCR2^+$ cells. Columns show the percentage of each subpopulation out of total monocyte population. The PBMC bar represents the distribution of monocyte sub-population in Peripheral Blood Mononuclear Cells isolated from a fresh blood donation separated using Ficol gradient. The CD14 column represents the distribution of monocyte sub-population following positive selection of CD14 positive cells by using CD14 antibodies conjugated to magnetic micro beads; the CCR2 depletion bar represents the distribution of monocyte sub-population following negative selection of CCR2 positive cells and positive selection of CD14 positive cells.

As can be seen from FIG. 5, the CCR2$^+$ cell depletion reveals an enrichment of the CD14$^{dim}$CD16$^+$ subpopulation by about 9 folds (from 8% to 73%) and enrichment of the CD14$^+$CD16$^+$ subpopulation by 10 folds (from 1% to 10%) while reducing the CD14$^+$CD16$^+$ subpopulation by about 5 folds (from 91% to 17%).

Figure 6:
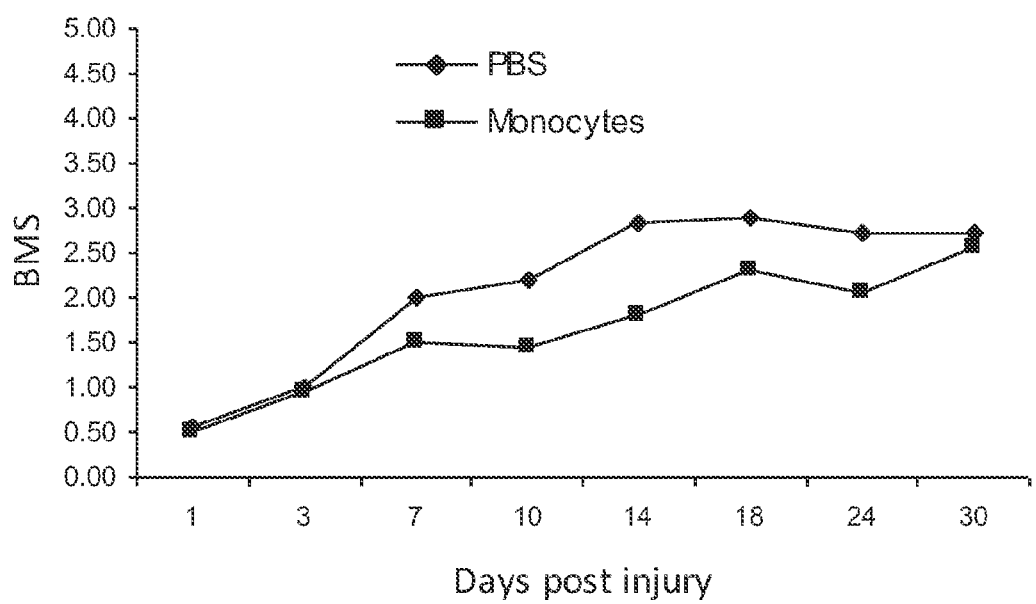
FIG. 6 shows that ICV injection of blood derived monocytes enriched for $CD14^{dim}CD16^+$ cells by depletion of the $CCR2^+$ cells failed to improve recovery from SCI. Moreover there is a tendency of worsening in the functional outcome; the Basso Mouse Scale (BMS) score is lower in the treated animals (monocytes) than the control animals injected with Phosphate Buffered Saline (PBS).

To examine the role of CD16$^+$ monocytes in the process of recovery following spinal cord injury, monocytes enriched for CD16$^+$ subpopulation were injected icy (into the CSF) into mice 4 days following injury. Hind-limb motor activity was monitored twice a week for up to 4 weeks post injury using the BMS scaling system. The control animals treated with the vehicle (PBS) showed a moderate spontaneous recovery with time, reaching about 2.5 on the BMS scale on average. The scores of the treated group (CD16+ enriched monocytes) were lower than the control group at each time point post injury indicating that their motor activity was reduced in comparison to the control group. We concluded that this sub-population, upon injection into the CSF of the animals at day 4 post SCI attenuates the spontaneous recovery (FIG. 6).

Contrary to the destructive effect on recovery that we found for CD16$^+$ monocytes, treatment with total monocytic subpopulations was beneficial for recovery from spinal cord injury, depending on the method of isolation (FIG. 7).

Discussion. For monocyte isolation, we used MACS technology developed by Miltenyi Biotec which is based on magnetic separation. In principle, the blood sample is labeled with magnetic microbeads conjugated to different antibodies. Cells are loaded onto a MACS column placed in a magnetic field. The magnetically labeled cells are retained within the column while the unlabeled cells run through. The retained cells can be eluted by removing the column from the magnetic field, named as positive selection. The unlabeled fraction, named as negative selection, can be collected too.

Monocytes were isolated using two approaches; positive or negative selection. For positive selection we used Miltenyi's CD14 microbeads and for negative selection we used Miltenyi's Monocyte Isolation Kit II. Apparently, monocytes that were isolated using negative selection show better and more consistence beneficial effects on animal's recovery from spinal cord injury than cells isolated via positive selection.

In summary, with respect to treatment following spinal cord injury, CD16 can be used as a marker to distinguish between beneficial (CD16−) and destructive (CD16+) blood monocytes. CD16− monocytes are known as classical monocytes and the CD16$^+$ as the proinflammatory monocytes that account for only 10% of all monocytes.

Example 4

Injection of a Monocyte Sub-population, Depleted of CD3, CD19, CD56 and CD16 Cells, into the CSF Promotes Functional Recovery in Mice Following Spinal Cord Injury In light of the above observations, we developed a procedure for isolation of CD16− monocytes using the MACS negative selection procedure. PBMCs were labeled with microbeads conjugated to CD3, CD19 and CD56 to deplete the T-cells, B-cells and NK cells. The unlabeled cells which passed through the magnetic column were collected. This fraction was labeled with CD16 microbeads and loaded again on the magnetic column. The cells that passed through the column were collected and stained for analysis in the FACS with CD14 and CD16 fluorescent antibodies. The left figure represents the PBMC before isolation (FIG. 8A) and the right figure (FIG. 8B) represents the final product following negative selection as described above. In the PBMCs, 19% of total live cells are monocytes (CD14+). Out of the monocytes, about 10% are CD16+. In the final product about 90% of live cells are monocytes out of which CD16+ is less than 0.1%.

The two sub-populations were shown to reach different stages of maturation following in-vitro stimulation (Carmen Sánchez-Torres, et. al. CD16+ and CD16− human blood monocyte subsets differentiate in vitro to dendritic cells with different abilities to stimulate CD4+ T cells. Int. Immunol. (2001) 13 (12): 1571-1581) and thus it may explain the different effect on the injured spinal cord.

We then examined the effect of the above described sub-population on reducing functional deficits following spinal cord injury in CD1-nude mice. The mice were subjected to a controlled severe spinal cord injury using the OSU ESCID contusion device (Ma M, Basso DM, Walters P, Stokes BT, Jakeman LB. Behavioral and histological outcomes following graded spinal cord contusion injury in the C57Bl/6 mouse. Exp Neurol. 2001 June; 169(2):239-54). Cells or PBS were applied to the CSF via ICV injection on day 4 post injury. Locomotor recovery after SCI was measured twice a week for 4 weeks post injury using the Basso Mouse Scale for Locomotion (BMS).

Figure 9:
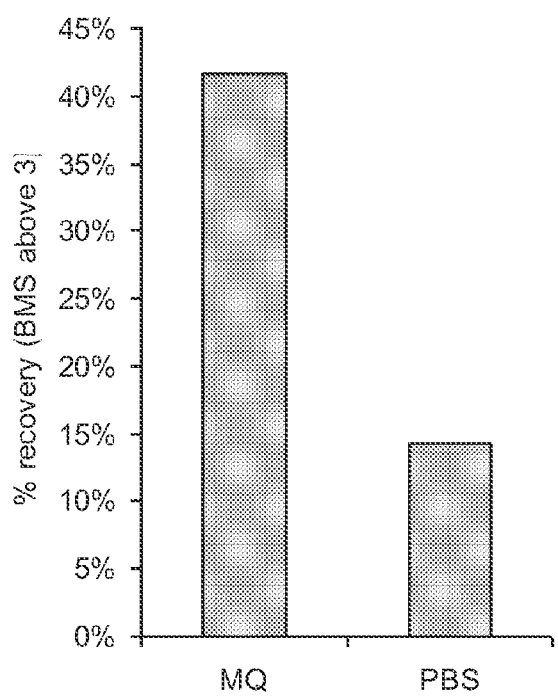
FIG. 9 shows the effect of injection of $0.5*10^6$ CD14++ CD16− skin-activated blood monocytes (MQ) or PBS to the CSF via ICV in mice subjected to a controlled severe spinal cord injury. Y-axis, % animals showing meaningful functional recovery of total animals tested.

Mice demonstrated slight spontaneous locomotor recovery at the first 3 weeks following injury. Recovery above 3 (plantar placing of the paw and weight support in stance was scored 4 in a scale from 0 to 9) in the BMS was considered a meaningful functional recovery. Treatment with the purified monocytes increased the rate of locomotor recovery of the animals (FIG. 9). 42% of the monocyte treated animals recovered (5 out of 12) as compared with 14% (2 out of 14) in the PBS treated control group.

All the references cited below are herein incorporated by reference in their entireties.

REFERENCES

Bomstein Y, Marder J.B., Vitner K, Smirnov I, Lisaey G, Butovsky O, Fulga V, Yoles E. (2003) Features of skin-coincubated macrophages that promote recovery from spinal cord injury. Journal of Neuroimmunology 142:10-16

Cros J, Cagnard N, Woollard K, Patey N, Zhang SY, Senechal B, Puel A, Biswas SK, Moshous D, Picard C, Jais JP, D'Cruz D, Casanova JL, Trouillet C, Geissmann F. Human CD14dim monocytes patrol and sense nucleic acids and viruses via TLR7 and TLR8 receptors. Immunity. 2010 Sep. 24; 33(3):375-86

Knoller N, Auerbach G, Fulga V, Zelig G, Attias J, Bakimer R, Marder J.B., Yoles E, Belkin M, Schwartz M, and Hadani M (2005) Clinical experience using incubated autologous macrophages as a treatment for complete spinal cord injury: Phase I study results J Neurosurg Spine 3:173-181.

Shechter R, London A, Varol C, Raposo C, Cusimano M, Yovel G, Rolls A, Mack M, Pluchino S, Martino G, Jung S, Schwartz M. (2009) Infiltrating blood-derived macrophages are vital cells playing an anti-inflammatory role in recovery from spinal cord injury in mice. 6(7).

The invention claimed is:

1. A method for treating a CNS injury comprising injecting into the CSF of an individual in need an effective amount of a subpopulation of peripheral blood mononuclear cells (PBMCs) substantially devoid of $CD3^+$ cells, $CD19^+$ cells, $CD56^+$ cells and $CD16^+$ cells.

2. The method according to claim 1, wherein said subpopulation of PBMCs is substantially enriched in $CD14^+$ cells.

3. The method according to claim 1, for treating neuronal degeneration caused by said CNS injury.

4. The method according to claim 3, wherein said treating comprises promotion of spinal cord tissue restoration, functional recovery, or both.

5. The method according to claim 1, for treating spinal cord injury.

6. The method according to claim 5, wherein said treating comprises promotion of spinal cord tissue restoration, functional recovery, or both.

7. The method according to claim 1, for treating a CNS injury is selected from the group consisting of blunt trauma, penetrating trauma, brain coup, contrecoup, trauma sustained during a neurosurgical operation, hemorrhagic stroke and ischemic stroke.

8. The method according to claim 7, wherein said treating comprises promotion of spinal cord tissue restoration, functional recovery, or both.

9. The method according to claim 1, wherein said PBMCs are autologous PBMCs.

10. The method according to claim 1, wherein the injecting into the CSF is via intrathecal injection, lumbar puncture (LP), injection through the Cisterna Magna (CM), intracerebroventricular (ICV) injection, or a combination thereof.

* * * * *